United States Patent [19]

Meanwell

[11] Patent Number: 5,187,188
[45] Date of Patent: Feb. 16, 1993

[54] OXAZOLE CARBOXYLIC ACID DERIVATIVES

[75] Inventor: Nicholas A. Meanwell, East Hampton, Conn.

[73] Assignee: Bristol-Myers Squibb Company, New York, N.Y.

[21] Appl. No.: 862,674

[22] Filed: Apr. 3, 1992

[51] Int. Cl.$^5$ .................... A61K 31/42; C07D 263/32
[52] U.S. Cl. .................... 514/374; 548/236; 548/235
[58] Field of Search .................... 514/374; 548/236

[56] References Cited

U.S. PATENT DOCUMENTS

| | | | |
|---|---|---|---|
| 3,578,671 | 5/1971 | Brown | 548/336 |
| 4,460,598 | 7/1984 | Lautenschlager et al. | 548/336 |
| 4,659,728 | 4/1987 | Lewis et al. | 514/374 |
| 4,775,674 | 10/1988 | Meanwell et al. | 546/82 |
| 4,785,012 | 11/1988 | Crews et al. | 514/374 |
| 4,962,117 | 10/1990 | Young et al. | 514/374 |
| 5,011,851 | 4/1991 | Meanwell | 514/398 |

FOREIGN PATENT DOCUMENTS

| | | | |
|---|---|---|---|
| 956963 | 10/1974 | Canada. | |
| 434034 | 6/1991 | European Pat. Off. | 548/236 |

OTHER PUBLICATIONS

D. L. Aldous, et al., *J. Org. Chem.*, 1151 (1960).
Davidson, et al., *J. Org. Chem.* 2: 328-334 (1937).
Armstrong, et al., *Br. J. Pharmac.*, 87: 543-551 (1986).

*Primary Examiner*—Donald G. Daus
*Attorney, Agent, or Firm*—Michelle A. Kaye

[57] ABSTRACT

A novel series of oxazole derivatives is disclosed in the Formula I wherein
Y and Z are independently hydrogen or together form a bond;
X is CN, $CO_2R^1$ or $CO.NR^2R^3$;
R and $R^1$ are independently or together H, Na, or $C_1$-$C_5$ lower alkyl;
$R^2$ and $R^3$ are independently or together H, or $C_1$-$C_5$ lower alkyl;
or alkali metal salt thereof.

The compounds are useful as inhibitors of ADP-induced blood platelet aggregation in human platelet-rich plasma.

39 Claims, 1 Drawing Sheet

FIG.1

OXAZOLE CARBOXYLIC ACID DERIVATIVES

BACKGROUND OF THE INVENTION

1. Field of the Invention

This invention relates to novel oxazole derivatives which are potent inhibitors of ADP-induced aggregation of human platelets.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischaemic heart disease, atherosclerosis, multiple sclerosis, intracranial tumors, thromboembolism, and hyperlipemia (Poplawski, et al, *J. Atherosclerosis Research*, 8, 721 (1968)).

Lautenschlager, et al., U.S. Pat. No. 4,460,598 issued Jul. 17, 1984 describe a series of triphenylimidazol-2-yloxyalkanoic acids having the formula (1)

wherein $R^1$, $R^2$, $R^3$, $R^4$, $R^5$ and $R^6$ each are H, halogen alkyl, alkoxy and trifluoromethyl; n is an integer of 1 to 10 and $R^7$ is H, alkali metal ions, alkyl or benzyl group. The compounds of U.S. Pat. No. 4,460,598 are reportedly useful in the treatment of thromboembolic, inflammatory and/or atherosclerotic disease in man. A particularly preferred member of the series wherein $R^1$ to $R^6$ is hydrogen, n is 7 and $R^7$ is sodium (identified in the art as octimibate sodium) has been described as possessing anti-aggregator activity.

Meanwell, N. A., European Patent Application 434034 further describes oxazole derivatives having formula (2) or (3)

wherein n is 7–9 and R is hydrogen or lower alkyl wherein $R^1$ is phenyl or thienyl; $R^2$ is hydrogen, lower alkyl or together with $CO_2$ is tetrazol-1-yl; X is a divalent connecting group; and Y is a divalent connecting group attached to the 3-or 4-phenyl position. Compounds of formulas (2) and (3) are useful as inhibitors of mammalian blood platelet aggregation. Among the compounds disclosed in the compounds of formula (4) identified as D. L. Aldous, et al., *J. Org. Chem.*, 1151 (1960) describe the chemistry of styruloxazoles of the formula (5)

wherein R is hydrogen, p-methoxy, o-hydroxy and 3,4-methylendioxy.

Brown, U.S. Pat. No. 3,578,671 describes a class of oxazole-2-polycarbon aliphatic monocarboxylic acids arylated at the 4- and/or 5-position in the oxazole ring of the formula (6)

in which each of the substituents $R^2$ and $R^3$ is a member of the group consisting of unsubstituted phenyl, naphthyl, thienyl and furyl radicals and phenyl radicals substituted by substituents selected from the group consisting of halogen, lower alkyl, lower alkoxy, nitro and trifluoromethyl radicals; and wherein $R^1$ is selected from the group consisting of carboxyalklyl- and carboxyalkenyl radicals each containing from 2 to 5 carbon atoms and the amides, hydroxamic acid derivatives, lower alkyl esters and lower alkanoyloxy-lower-alkyl esters thereof. The compounds of U.S. Pat. No. 3,578,671 include the clinically effective anti-inflammatory agent known generically as oxaprozin ($R^2=R^3=$phenyl, $R^1=(CH_2)_2CO_2H$).

SUMMARY OF THE INVENTION

The present invention is concerned with oxazole derivatives having Formula I infra., which are inhibitors of ADP-induced aggregation of human blood platelets in platelet rich plasma.

Another embodiment of the invention relates to the alkali metal salts of carboxylic acids of Formula I (R is hydrogen).

A further embodiment concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I or an alkali metal salt thereof to a mammal in need of such treatment.

DETAILED DESCRIPTION OF THE INVENTION

The compounds of the instant invention are characterized by Formula I

Formula I wherein
Y and Z are independently hydrogen or together form a bond;
X is CN, $CO_2R^1$ or $CO.NR^2R^3$;
R and $R^1$ are independently or together H, Na, or $C_1$-$C_5$ lower alkyl;
$R^2$ and $R^3$ are independently or together H, or $C_1$-$C_5$ lower alkyl;
or alkali metal salt thereof.

It is understood that as used herein limitations of Formula I are defined as follows:

The term "$C_1$-$C_5$ lower alkyl" refers to a branched or unbranched saturated hydrocarbon chain containing from 1-5 carbon atoms, for example, methyl, ethyl, n-propyl, iso-propyl, n-butyl, secondary butyl and tertiary butyl.

The symbol "Ph" represents phenyl.

The term "alkali metal salts" comprehends the alkali metals and most preferably sodium and potassium.

When Y and Z together form a bond, geometrical isomers are possible. The invention encompasses both geometrical isomeric forms.

According to the present invention, the compounds characterized by Formula I were prepared as outlined is Schemes 1, 2 and 3.

Acylation of benzoin (1) with ethyl malonyl chloride (2) in dichloromethane ($CH_2Cl_2$) using pyridine as the base provided ester 3. Exposure of the crude product to an excess of ammonium acetate in acetic acid at reflux (Davidson et al., J. Org. Chem. 2 328-334 (1937)) furnished the known oxazole 4 (Canadian Patent No. 956,963, 1974) after chromatography. Ester 4 was employed as a precursor to all of the α-substituted esters and amides that constitute this study. Trans-esterification under acidic or basic conditions provided the corresponding methyl and iso-propyl esters while heating with ammonia, methylamine or dimethylamine in a sealed vessel afforded the respective amides. The intermediates 5 were condensed with an aldehyde 6 under Knoenvenagel conditions (piperidine/p-toluenesulfonic acid/toluene/reflux/azeotropic removal of water) to yield the adducts 7 as a mixture of geometrical isomers which were not separated. The ratio and identity of the (E) and (Z) isomers was determined by inspection of NMR spectral data. The choice of the ester moiety of 6 was dictated by the nature of the subsequent synthetic transformations. Condensation of 5 with 6, ($R^1$ is $CH_3$) allowed for isolation of 7, ($R^1$ is $CH_3$) which were hydrogenated over 10% palladium on charcoal (Pd-C) to provide the saturated methyl esters 9. For the dimethylamide 9j, saponification provided the acid 10g, (R is $N(CH_3)_2)$). For diesters 7, selectivity for ester hydrolysis was achieved by employing the acid-sensitive tert-butyl ester of 6 as a precursor to the acids 8, (R is isopropoxy ($O^ipr$), ethyl alcohol (OEt) or methoxy (OMe)). Treatment of 7, ($R^1$ is t-butyl), with trifluoroacetic acid provided acids 8 while hydrogenation over Pd-C furnished diesters 9, ($R^1$ is t-butyl) which were converted to acids 10 under acidic conditions. This synthetic protocol was also employed to synthesize the primary and mono-methyl amides of 8 and 10, (R is $NH_2$ and $NH.CH_3$). The diacid derived from 10 was isolated as its disodium salt by saponification of 9, (R is OEt, and $R^1$ is Me) using two equivalents of sodium hydroxide in aqueous methanol. Isolation of this acid as the disodium salt was deemed necessary due to the propensity of the free acid to suffer decarboxylation in related systems.

SCHEME 1

-continued
SCHEME 1

R[1] is H or lower alkyl, Na
R is OR[2] or NR[3]R[4]
R[2] is H, Na or lower alkyl
R[3] is H or CH$_3$
R[4] is H or CH$_3$

Figure 1:
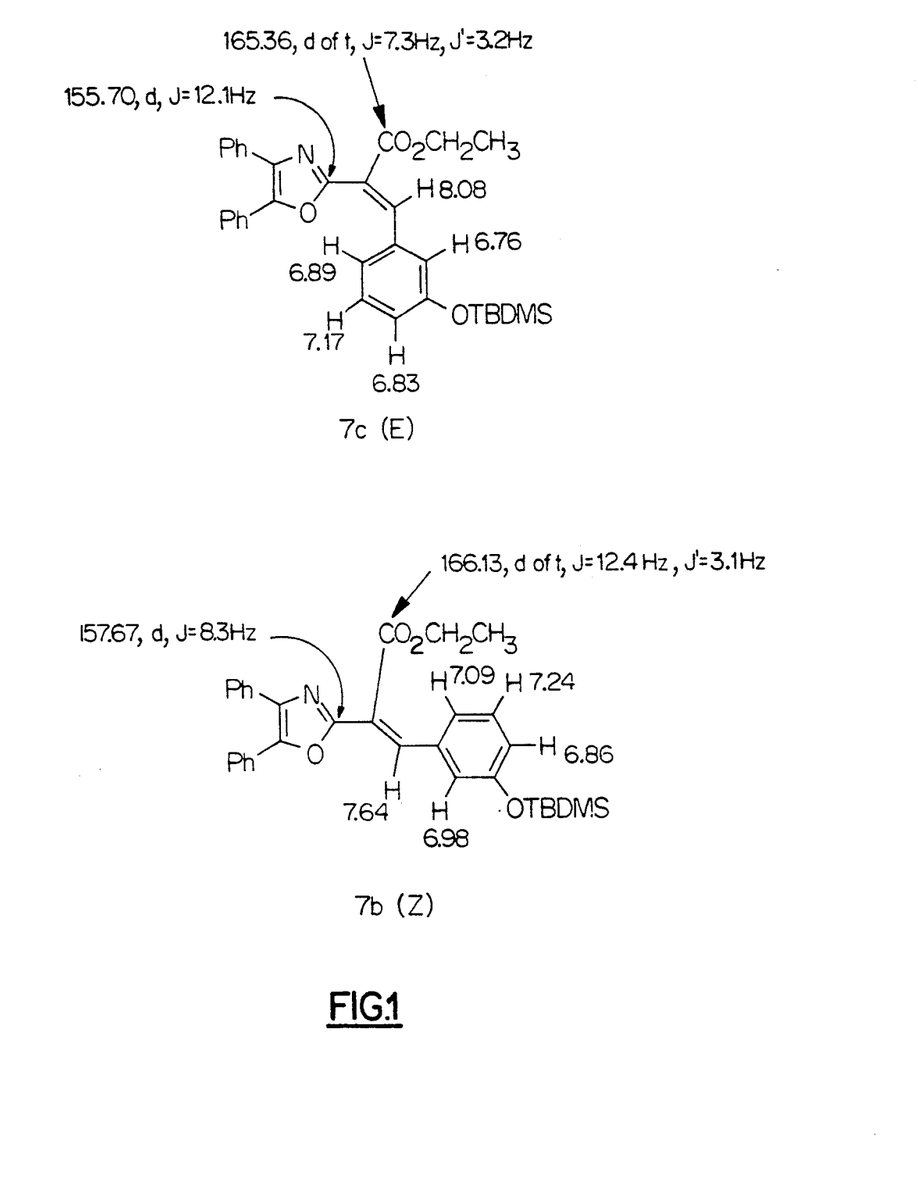
FIG. 1 shows the NMR data for compounds 7b and 7c.

The diesters 7b and 7c were prepared with a high degree of geometrical homogeneity as shown in Scheme 2. Condensation of 4 with the tert-butyldimethylsilyl (TBDMS) ether of 3-hydroxybenzaldehyde (11) provide a mixture of the adducts 12 and 13 which were separated by careful chromatography on silica gel. The less polar material was assigned the (Z) configuration, 7b, based on the observed long range $^1$H-$^{13}$C coupling in the fully-coupled $^{13}$C NMR spectrum, which complemented those recorded for the more polar material 7c, assigned the (E) geometry. The NMR data for these compounds is summarized in FIG. 1. Deprotection of 12 and 13, using tetra-n-butylamonium fluoride ((n-Bu)$_4$NF) in anhydrous tetrahydrofuran (THF) at −30° to −10° C., provided the geometrically isomeric phenols with excellent retention of stereochemical integrity. These were individually alkylated with methyl bromoacetate in acetonitrile at reflux using pulverized potassium carbonate as the base, to provide the diesters 7b and 7c.

SCHEME 2

1. piperidine/TsOH/PhCH$_3$/Δ
2. chromatograph

SCHEME 2

The α-substituted nitriles 16 and 17 were obtained as depicted in Scheme 3. Exposure of the bromide 14 (Aldous, et al., *J. Org. Chem.*, 25: 1151–1154 (1960)) to potassium cyanide gave the nitrile 15. Condensation of 15 with 6, $R^1$ is $CH_3$, provided a single adduct 16 identified as the (E) isomer based on long range coupling between the olefinic proton and the nitrile and oxazole-2-carbon atoms in the fully-coupled $^{13}C$ NMR spectrum. Alkaline hydrolysis of 16 provided 17 whilst reduction, using sodium borohydride in methanol, furnished 18, which was hydrolysed to acid 19.

SCHEME 3

SCHEME 3

In Vitro Inhibition of Human Platelet Aggregation

The aggregometer method of Born, G. V. R., *J. Physiol.*, (London), 162, 67-68, (1962) as modified by Mustard, J. F., et al., *J. Lab. Clin. Med.*, 64, 548-599, (1964) Was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140×g) from citrated (3.8%) human blood. All glassware used for preparation of PRP is silicon treated. ADP in final concentration of 0.5 mcg/mL or 0.05 mL of a collagen suspension prepared according to the method described by Evans, G., et al., *J. Exp. Med.*, 128, 877-894, (1968) was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 mcg/ml vs. ADP and 245 mcg/ml vs collagen. Results for 50% inhibition of ADP-induced aggregation are given hereinafter.

The compounds listed in Table 1 were evaluated as inhibitors of human platelet aggregation in vitro in platelet-rich-plasma (PRP) using 5.86 mM ADP as the inducing agent. The PRP was incubated with drug for about three minutes prior to the addition of the agonist. The extent of aggregation in the presence of various concentrations of test compounds was compared with that in vehicle controls. Dose-response curves were obtained and $IC_{50}$ values determined. The results are presented in Table 2. In this assay, the formula (4) compound half-maximally prevents aggregation at a concentration of 0.6 μg/mL.

TABLE 1

Physical Chemical Properties of α-substituted Oxazole Derivatives

| Compound # | M.P. | $IC_{50}$ in human PRP vs ADP, μg/mL |
|---|---|---|
| 7a | oil | >32 |
| 7b | oil | 10 |
| 7c | oil | 1 |
| 8a | 54–56 | 0.17 |
| 8b | 178–182 | 9 |

TABLE 1-continued

Physical Chemical Properties of α-substituted Oxazole Derivatives

| Compound # | M.P. | $IC_{50}$ in human PRP vs ADP, μg/mL |
|---|---|---|
| 9a | oil | >32 |
| 9b | oil | 0.75 |
| 10a | 140–145 | 0.06 |
| 10b | not taken | 7 |
| 7d | oil | 0.5 |
| 9c | oil | >32 |
| 9d | oil | 0.6 |
| 10c | 122–127 | 0.037 |
| 7e | oil | >32 |
| 7f | oil | 5 |
| 9e | oil | >32 |
| 9f | oil | 3.5 |
| 10d | 88–93 | 0.6 |
| 7g | 69–76 | 2.5 |
| 8c | 226.5–229 | >32 |
| 9g | 53–63 | >32 |
| 9h | 48–53 | >32 |
| 10e | 80–84 | 1.7 |
| 7h | foam | 1.3 |
| 8d | 166–171 | 7 |
| 9i | 109–113 | 3.5 |
| 10f | 85–89 | 0.32 |
| 7i | 159–162.5 | >32 |
| 8e | 223–226 | 5.8 |
| 9j | oil | 16 |
| 10g | 76–80 | 1.7 |
| 16 | 152–153.5 | 8 |
| 17 | 154–159 | 0.11 |
| 18 | resin | 0.36 |
| 19 | 166–171 | 0.20 |

The Formula I compounds or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient. Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

Ethyl 4,5-diphenyl-2-oxazoleacetate (4)

Ethyl malonyl chloride (25.68 g, 0.17 mol) was added dropwise to a stirred solution of benzoin (32.90 g, 0.155 mol), pyridine (13.53 g, 0.17 mol) and 4-dimethylaminopyridine (catalytic quantity) in $CH_2Cl_2$ (300 mL) maintained at about 10° C. with an ice-water bath. The mixture was stirred for about 30 minutes at about 10° C. and about 2 hours at room temperature before being concentrated in vacuo. Glacial acetic acid (600 mL) and ammonium acetate (59.68 g, 0.775 mol) were added to the residue and the mixture heated to reflux. After about 2 hours, the solution was diluted with $CH_2Cl_2$, washed with water (3×) and saturated sodium chloride solution and dried over sodium sulfate. Evaporation of the solvent left an oil which was chromatographed on a column of silica gel using a mixture of hexanes and ethyl acetate (17:3) as eluent to give ethyl 4,5-diphenyl-2-oxazoleacetate (29.26 g, 61%). Recrystallization from a mixture of hexanes and $CH_2Cl_2$ (8:1) gave pure material, mp 71°–72° C. IR (KBr) 1740 0($CO_2Et$) cm$^{-1}$; $^1$H NMR ($CDCl_3$) δ1.26 (3H, t, J=7Hz, $CO_2CH_2\underline{CH}_3$), 3.91 (2H, s, $\underline{CH}_2CO_2Et$), 4.22 (2H, q, J=7Hz, $OC\underline{H}_2$), 7.25 to 7.45 (6H, m, aromatic $\underline{H}$), 7.50 to 7.75 (4H, m, aromatic $\underline{H}$); MS m/z 308 (MH$^+$).

Anal. Calcd. for $C_{19}H_{17}NO_3$: C, 74.26; H, 5 58; N, 4.56. Found: C, 74.15; H, 5.77; N, 4.74.

EXAMPLE 2

(E) and (Z)-Ethyl α-[[3-[[(1,1-dimethylethoxy)carbonyl]methoxyl]phenyl]methylene]-4,5-diphenyl-2-oxazoleacetate (7a)

A mixture of ethyl 4,5-diphenyl-2-oxazoleacetate (25.00 g, 81 mmol), 1,1-dimethylethyl(3-formylphenoxy)acetate (19.22 g, 81 mmol), piperidine (0.69 g, 8 mmol), p-toluenesulfonic acid (catalytic quantity) and toluene (200 mL) was heated at reflux under a Dean-Stark trap. After about 18 hours, the mixture was cooled, diluted with $CH_2Cl_2$ and washed with water (2×) and saturated NaCl solution before being dried over $Mg_2SO_4$. Evaporation of the solvent left an oil which was subjected to chromatography on a column of silica gel. Elution with a mixture of hexanes and ethyl acetate (4:1) afforded the title compound (41.49 g, 97%) as an oil. IR (film) 1760, 1730 ($CO_2R$) cm$^{-1}$; $^1$H NMR ($CDCl_3$) δ1.28 to 1.36 (4H, overlapping triplets, $OCH_2\underline{CH}_3$), 1.37 and 1.47 (18H, singlets, $C(\underline{CH}_3)_3$), 4.30 and 4.50 (4H, singlets, $O\underline{CH}_2CO_2{}^tBu$), 4.33 (2H, q, J=7Hz, $OC\underline{H}_2CH_3$ of one isomer), 4.41 (2H, q, J=7Hz, $OC\underline{H}_2CH_3$ of other isomer), 6.70 to 7.70 (29H, m, aromatic $\underline{H}$+1 olefinic $\underline{H}$), 8.07 (1H, s, olefinic $\underline{H}$ of (E) isomer); MS m/z 526 (MH$^+$).

Anal. Calcd. for $CH_{32}H_{31}NO_6$: C, 73.14; H, 5.91; N, 2.67. Found: C, 73.27; H, 5.94, N, 2.60.

EXAMPLE 3

Ethyl α-[[3-[[(1,1-dimethylethoxy)carbonyl]methoxyl]-phenyl[methyl-4,5-diphenyl-2-oxazoleacateate, (9a)

A solution of (E) and (Z)-ethyl α-[[3-[[(1,1-dimethylethoxy)carbonyl]methoxy]phenyl]methylene-4,5-diphenyl-2-oxazoleacetate (2.15 g, 4 mmol) in ethyl acetate (75 mL) was hydrogenated at 30 psi over 10% Pd on C (0.30 g) in a Parr hydrogenation apparatus. After hydrogen uptake ceased, the mixture was filtered through Celite and concentrated to leave an oil which was subjected to chromatography on a column of silica gel. Elution with a mixture of hexanes and EtOAc (9:1) afforded the title compound (1.05 g, 48%). IR (film) 1745 cm$^{-1}$; $^1$H NMR (CDCl$_3$) δ1.19 (3H, t, J=7Hz, OCH$_2$CH$_3$), 1.45 (9H, s, OC(CH$_3$)$_3$), 3.44 (2H, overlapping AB quartets, CH$_2$-aryl), 4.18 (3H, q, CH.CO$_2$CH$_2$CH$_3$), 4.43 (1H, s, OCH$_2$), 6.72 (1H, dd, J=7Hz, J'=2Hz, aryl H ortho to O), 6.75 (1H, d, J=2Hz, aryl H ortho to O), 6.86 (1H, d, J=7Hz, aryl H para to O), 7.17 (1H, t, J=7Hz, aryl H meta to O), 7.25 to 7.42 (6H, m, aromatic H), 7.50 to 7.70 (4H, m, aromatic H); MS m/z 528 (M+).

Anal. Calcd. for CH$_{32}$H$_{33}$NO$_6$.0.15H$_2$O: C, 72.48; H, 6.33; N, 2.65; H$_2$O, 0.51. Found: C, 72.37; H, 6.50; N, 2.69; H$_2$O, 0.44.

EXAMPLE 4

(E) and (Z) Ethyl α-[[3-carboxymethoxy)phenyl]methylene]-4,5-diphenyl-2-oxazole acetate, (8a)

A solution of ethyl α-[[3-[[1,1,-dimethylethoxy)carbonyl]methoxy]phenyl]methylene]-4,5-diphenyl-2-oxazoleacetate (0.70 g, 1.3 mmol) in CF$_3$CO$_2$H (6 mL) was stirred at room temperature for about 1 hour. The mixture was diluted with EtOAc and water and the organic layer separated, washed with water and saturated brine and dried over Na$_2$SO$_4$. Evaporation of the solvent left an oil which was chromatographed on a column of silica gel using a mixture of CHCl$_3$ and MeOH (24:1) as eluent to give the title compound (0.41 g, 66%) as a yellow foam, mp 54°-56° C. IR (KBr) 1725 cm$^{-1}$; $^1$H NMR (CDCl$_3$) δ1.20 to 1.38 (6H, overlapping t, OCH$_2$CH$_3$), 4.32 (2H, q, J=7Hz, OCH$_2$), 4.39 (2H, q, J=7Hz, OCH$_2$), 4.43 (2H, s, OCH$_2$CO$_2$H), 4.62 (2H, s, OCH$_2$), 6.70 to 7.75 (11H, m, aromatic H+olefinic H of (Z) isomer), 8.08 (1H, s, olefinic H of (E) isomer), 8.65 (1H, bs, CO$_2$H); MS m/z 470 (M+).

Anal. Calcd. for C$_{28}$H$_{22}$NO$_6$.0.15H$_2$O: C, 71.23; H, 4.98; N, 2.97; H$_2$O, 0.57. Found C, 71.22; H, 5.18; N, 2.87; H$_2$O, 0.49.

EXAMPLE 5

Ethyl α-[[3-hydroxy-2-oxoethoxyl]phenyl]methyl]-4,5-diphenyl-2-oxazole acetate, (10a)

A mixture of ethyl α-[[3-[[(1,1-dimethylethoxy)carbonyl]methoxy]phenyl]methyl]-4,5-diphenyl-2-oxazoleacetate (3.74 g, 7 mmol) in CF$_3$CO$_2$H (17 mL) was stirred at room temperature. After about 1 hour, the mixture was diluted with water and extracted with EtOAc (3×). The combined extracts were washed with saturated NaCl solution and dried over Na$_2$SO$_4$. Evaporation of the solvent left an oil which was subjected to chromatography on a column of silica gel using a mixture of CHCl$_3$ and MeOH (97:3) as eluent. Elution gave the title compound as a yellow solid (2.09 g, 62%), mp 140°-145° C. IR (KBr) 1740 cm$^{-1}$; $^1$H NMR (CDCl$_3$) δ1.19 (3H, t, J=7Hz, CO$_2$CH$_2$CH$_3$), 3.43 (2H, doublet of ABq, J=14Hz, J'=7Hz, CH$_2$-aryl), 4.17 (2H, q, J=7Hz, OCH$_2$), 4.39 (1H, t, J=7Hz, CH.CO$_2$Et), 4.57 (2H, s, OCH$_2$), 6.75 (1H, dd, J=7H, J'=2Hz, aromatic H ortho to O), 6.84 (2H, m, aromatic H ortho and para to O), 7.16 (1H, t, J=7Hz, aromatic H meta to O), 7.30 to 7.75 (10H, m, aromatic H); MS m/z 472 (M+).

Anal. Calcd. for C$_{28}$H$_{25}$NO$_6$.1.2H$_2$O: C, 68.20; H, 5.61; N, 2.85; H$_2$O, 4.38. Found: C, 68.02; H, 5.27; N, 2.68; H$_2$O, 2.03.

EXAMPLE 6

(E) and (Z)-α [[3-(2-hydroxy-2-oxoethyl)phenyl]methylene]-4,5-diphenyl-2-oxazole acetic acid, (8b)

A mixture of ethyl α-[[3- carboxymethoxy)phenyl]methylene]-4,5-diphenyl-2-oxazoleacetate (2.32 g, 5 mmol), 3N NaOH solution (6.6 mL, 20 mmol) and methanol (125 mL) was heated at reflux on a steam bath for about 10 minutes. The mixture was cooled, concentrated in vacuo and the residue diluted with water and 2N HCl solution until pH=2. The mixture was extracted with CH$_2$Cl$_2$ (3×), the combined extracts washed with saturated NaCl solution, dried over Na$_2$-

SO4 and the solvent evaporated to leave a solid. Dissolution in CH2Cl2 followed by the addition of hexanes gave a yellow solid which was recrystallised from a mixture of CH2Cl2, hexanes and MeOH (3:2:1) to furnish the title compound (0.85 g, 39%), mp 178°-182° C., as a 3:2 mixture of (E) and (Z) isomers. IR (KBr) 3060, 2920, 1740, 1720 cm−1; 1H NMR (DMSO-d6) δ4,56 (2H, s, OCH2), 4.69 (2H, s, OCH2), 6.80 to 7.00 (2H, m, aryl H ortho to O), 7.20 to 7.70 (2H, m, aryl H+olefinic H), 8.08 (1H, s, olefinic H cis to acid); MS m/z 442 (M+).

Anal. Calcd. for C26H19NO6.0.15 H2O: C, 70.32; H, 4.39; N, 3.16; H2O, 0.61. Found: C, 70.04; H, 4.30; N, 3.05; H2O, 0.34.

EXAMPLE 7

Ethyl α-[(3-[(methoxycarbonyl)methoxyl]phenyl]-methyl]-4,5-diphenyl-2-oxazole acetate (9b)

Prepared from a 1:1 (Z):(E) mixture of ethyl α-[[3-(2-methoxy-2-oxoethoxy)phenyl]-methylene]-4,5-diphenyl-2-oxazoleacetate (0.76 g, 1.6 mmol) by hydrogenation over 10% Pd on C (0.08 g) in EtOAc (50 mL) using a Parr hydrogenation apparatus. Purification was effected by repeated chromatography on silica gel using a mixture of hexanes and ethyl acetate (6:1) as eluent to give the title compound as an oil (0.39 g, 51%). IR (film) 1760, 1740 cm−1; 1H NMR (CDCl3) δ1.19 (3H, t, J=7Hz, OCH2CH3), 3.45 (2H, d of ABq, CH2Ar), 3.75 (3H, s, OCH3), 4.18 (3H, m, OCH2CH3+CH.CO2Et), 4.55 (2H, s, OCH2), 6.73 (1H, dd, J=7Hz, J'=2Hz, aromatic H ortho to O), 6.78 (1H, d, J=2Hz, aromatic H ortho to O), 6.87 (1H, d, J=7Hz, aromatic H para to O), 7.18 (1H, t, J=7Hz, aromatic H meta to O), 7.27 to 7.40 (6H, m, aromatic H), 7.50 to 7.70 (4H, m, aromatic H); MS m/z 486 (M+).

Anal. Calcd. for C29H27NO6: C, 71.75; H, 5.57; N, 2.89. Found: C, 71.77; H, 5.82; N, 2.91.

EXAMPLE 8

(E) and (Z) Ethyl α-[[3-[(1,1-dimethylethyl) dimethylsiloxyl]phenyl]methylene-4,5-diphenyl-2-oxazoleacetate, (12) and (13)

A mixture of ethyl 4,5-diphenyl-2-oxazoleacetate (10.33 g, 33 mmol), 3-[dimethyl(1,1-dimethylethyl)silyl-]oxybenzaldehyde 7.94 g, 33 mmol), piperidine (0.29 g, 33 mmol), p-toluenesulfonic acid (catalytic quantity) and toluene (120 mL) was heated at reflux under a Dean-Stark trap. After about 3 hours, the solvent was evaporated and the residual oil chromatographed repeatedly on a column of silica gel using a mixture of hexanes and EtOAc (19:1) as eluent. The less polar material was identified as the (Z) isomer 12 (5.27 g, 30%), mp 97°-100° C. IR (KBr) 1730 cm−1; 1H NMR (CDCl3) δ0.22 (6H, s, Si(CH3)2), 1.00 (9H, s, C(CH3)3), 1.34 (3H, t, J=7Hz, OCH2CH3), 4.43 (2H, q, J=7Hz, OCH2), 6.86 (1H, dd, J=7Hz, J'=2Hz, aromatic H ortho to O), 6.98 (1H, d, J=2Hz, aromatic H ortho to O), 7.09 (1H, d, J=7Hz, aromatic H para to O), 7.24 (1H, t, J=7Hz, aromatic H meta to O), 7.27 to 7.45 (6H, m, aromatic H), 7.58 to 7.73 (5H, m, aromatic H+olefinic H); MS m/z 526 (MH+).

Anal. Calcd. for CH32H35NO4Si: C, 73.12; H, 6.72; N, 2.67. Found: C, 73.07; H, 6.65; N, 2.59.

The more polar material was identified as the (E) isomer 13 (5.78 q, 32%). IR (film) 1725 cm−1; 1H NMR (CDCl3) δ0.05 (6H, s, Si(CH3)2), 0.86 (9H, s, C(CH3)3), 1.32 (3H, t, J=7Hz, OCH2CH3), 4.32 (2H, q, J=7Hz, OCH2), 6.76 (1H, t, J=2Hz, aromatic H ortho to O), 6.83 (1H, dt, J=8Hz, J'=2Hz, aromatic H ortho to O), 6.89 (1H, d, J=8Hz, aromatic H para to O), 7.17 (1H, t, J=8Hz, aromatic H meta to O), 7.25 to 7.40 (6H, m, aromatic H), 7.66 to 7.72 (2H, m, aromatic H), 8.08 (1H, s, olefinic H); MS m/z 526 (MH+).

Anal. Calcd. for CH32H35NO4Si: C, 73.12; H, 6.72; N, 2.67. Found: C, 73.39; H, 6.76; N, 2.60.

EXAMPLE 9

(Z)-Ethyl-α-[[3-(2-methoxy-2-oxoethoxy)phenyl]methylene]-4,5-diphenyl-2-oxazole acetate, (7b)

A solution of (Z)-ethyl α-[[3-[[[dimethyl(1,1-dimethyl)ethyl]silyl]oxy]phenyl]methylene]-4,5-diphenyl-2-oxazoleacetate (1.87 g, 3.6 mmol) in anhydrous THF (60 mL) maintained under an atmosphere of nitrogen was cooled to −30° C. and tetra-n-butylammonium fluoride (1.02 g, 4 mmol) in THF (3.92 mL) added dropwise. The mixture was stirred for about 30 minutes before being diluted with satd. NH4Cl solution and extracted with Et2O. The organic extracts were washed with satd. NaCl solution, dried over Na2SO4 and concentrated in vacuo to leave an oil (1.46 g) which was dissolved in CH3CN (70 mL). Methyl bromoacetate (0.60 g, 3.9 mmol), potassium carbonate (0.59 g, 4.3 mmol) and potassium iodide (catalytic quantity) were added and the mixture heated at reflux for about 1 hour. The mixture was filtered through Celite, concentrated and the residual oil subjected sequentially to column and radial chromatography over silica gel using CHCl3 as eluent to give 7b (0.97 g, 56%). IR (film) 1765, 1740, 1215 cm−1; 1H NMR (CDCl3) δ1.20 (3H, t, J=7Hz, OCH2CH3), 3.79 (3H, s, CO2CH3), 4.39 (2H, q, J=7Hz, OCH2CH3), 4.62 (2H, s, OCH2), 6.90 (1H, dd, J=7Hz, J'=2Hz, aromatic H ortho to O), 6.98 (1H, d, J=2Hz, aromatic H ortho to O), 7.10 (1H, d, J=7Hz, aromatic H para to O), 7.23 (0.45H, s, CHCl3), 7.25 to 7.45 (7H, m, aromatic H), 7.55 to 7.73 (4H, m, aromatic H), 7.62 (1H, s, olefinic H); MS m/z 484 (MH+).

Anal. Calcd. for C29H25NO6.0.3H2O.0.15CHCl3: C, 69.09; H, 5.13; N, 2.77; H2O, 1.07 Found: C, 69.20; H, 5.09; N, 2.62; H2O, 1.16.

EXAMPLE 10

(E)-Ethyl α-[[3-(2-methoxy-2-oxoethoxy)phenyl]methylene]-4,5-diphenyl-2-oxazole acetate, (7c)

Prepared from the TBDMS phenol (2.88 g, 5.5 mmol) via an analogous procedure to that described for 7b to afford the title compound (2.33 g, 100%). IR (film) 1760, 1715, 1450 cm$^{-1}$; $^1$H NMR (CDCl$_3$) d 1.27 (3H, t, J=7Hz, OCH$_2$CH$_3$), 3.59 (3H, s, OCH$_3$), 4.28 (2H, q, J=7Hz, OCH$_2$CH$_3$), 4.39 (2H, s, OCH$_2$),5.22 (0.4H, s, CH$_2$Cl$_2$), 6.73 (1H, d, J=2Hz, aromatic H ortho to O), 6.85 to 6.95 (2H, m, aromatic H ortho and para to O), 7.19 (1H, t, J=7Hz, aromatic H meta to O), 7.20 to 7.40 (6H, m, aromatic H), 7.53 (2H, m, aromatic H) 7.68 (2H, m, aromatic H), 8.03 (1H, s, olefinic H); MS m/z 484 (MH$^+$).

Anal. Calcd. for C$_{29}$H$_{25}$NO$_6$.0.1H$_2$O.0.2CH$_2$Cl$_2$: C, 69.83; H, 5.14; N, 2.79; H$_2$O, 0.36. Found: C, 69.74; H, 5.10; N, 2.78; H$_2$O, 0.30.

EXAMPLE 11

α-[[3-(2-Hydroxy-2-oxoethoxy)phenyl]methyl]-4,5-diphenyl-2-oxazoleacetic acid, disodium salt, (10b)

A mixture of ethyl α-[[3-[(methoxycarbonyl) methoxy]phenyl]methyl]-4,5-diphenyl-2-oxazoleacetate (1.50 g, 3.1 mmol), sodium hydroxide (0.245 g, 6.1 mmol) and methanol 15 mL) was stirred at room temperature for about 24 hours and at reflux for about 18.5 hours. The solvent was evaporated to leave the title compound as a solid (1.55 g, 100%). IR (KBr) 3400, 1610 cm$^{-1}$; $^1$H NMR (D$_2$O) δ3.24 (1H, dd, J=13Hz, J'=13Hz, CH$_2$Ar), 3.38 (1H, dd, J=13Hz, J'=6Hz, CH$_2$Ar), 4.06 (1h, dd, J=13Hz, J'=6Hz, CH.CO$_2$Na), 4.26 (2H, s, OCH$_2$), 6.60 (1H, dd, J=7Hz, J'=2Hz, aromatic H ortho to O), 6.70 to 6.95 (2H, m, aromatic H ortho and para to O), 7.00 to 7.40 (11H, m, aromatic H); MS m/z 342 (MH$^+$—CO$_2$ and CH$_2$CO$_2$).

Anal. Calcd. for C$_{26}$H$_{19}$NO$_6$Na$_2$.0.65H$_2$O: C, 62.57; H, 4.10; N, 2.81; H$_2$O, 2.35. Found: C, 62.95; H, 4.43; N, 2.58; H$_2$O, 3.22. 12690060.

EXAMPLE 12

Methyl 4,5-diphenyl-2-oxazoleacetate mp 87°–91° C. IR (KBr) 1750 cm$^{-1}$; $^1$H NMR (DCl$_3$) δ3.74 (3H, s, OCH$_3$), 3.91 (2H, s, CH$_2$CO$_2$CH$_3$), 7.22 to 7.40 (6H, m, aromatic H), 7.52 to 7.65 (4H, m, aromatic H); MS m/z 294 (MH$^+$).

EXAMPLE 13

Methyl (E) and (Z) α-[[3-(2-methoxy-2-oxoethoxy)phenyl]methylene]-4,5-diphenyl-2-oxazoleacetate, (7d)

Isolated as a 1:1 mixture of geometrical isomers after column chromatography on silica gel using hexanes and EtOAc (4:1) as eluent (0.69 g, 80%). IR (film) 1760, 1730 cm$^{-1}$; $^1$H NMR (CDCl$_3$) δ3.69 (3H, s, OCH$_3$), 3.84 (3H, s, OCH$_3$), 3.90 (3H, s, OCH$_3$), 3.96 (3H, s, OCH$_3$), 4.47 (2H, s, OCH$_2$), 4.68 (2H, s, OCH$_2$), 6.80 to 7.50 (20H, m, aromatic H), 7.50 to 7.80 (8H, m, aromatic H), 7.72 (1H, s, olefinic H of (Z) isomer), 8.15 (1H, s, olefinic H of (E) isomer); MS m/z 470 (MH$^+$).

Anal. Calcd. for C$_{28}$H$_{23}$NO$_6$: C, 71.64; H, 4.90; N, 2.99. Found: C, 71.65; H, 4,82; N, 2.90.

Compound of Example 14 was prepared in a manner similar to that of Example 15.

EXAMPLE 14

Methyl α-[[3-(2-(1,1-dimethylethoxy-2-oxoethoxy)phenyl]methyl]-4,5-diphenyl-2-oxazole acetate, (9c)

Isolated 1.06 g, 95% after hydrogenation of the unsaturated precursor over 10% Pd on C. IR (film) 1750 cm$^{-1}$; $^1$H NMR (CDCl$_3$) δ1.43 (9H, s, C(CH$_3$)$_3$), 3.42 (2H, d of AB q, J=14Hz, J'=7Hz, CH$_2$Ar), 3.68 (3H, s, CO$_2$CH$_3$), 4.20 (1H, t, J=7Hz, CHCO$_2$Me), 4.40 (2H, s, OCH$_2$), 6.70 (1H, dd, J=7Hz, J'=2Hz, aromatic H ortho to O), 6.74 (1H, d, J=2Hz, aromatic H ortho to O), 6.82 (1H, d, J=7Hz, aromatic H para to O), 7.15 (1H, t, J=7Hz, aromatic H meta to O), 7.25 to 7.40 (6H, m, aromatic H), 7.50 to 7.65 (4H, m, aromatic H); MS m/z 514 (MH$^+$).

Anal. Calcd. for C$_{31}$H$_{31}$NO$_6$: C, 72.50; H, 6.09; N, 2.73. Found: C, 73.06; H, 5.80; N, 2.86

EXAMPLE 15

Methyl α-[[3-(2-methoxy-2-oxoethoxy)phenyl]methyl]-4,5-diphenyl-2-oxazole acetate, (9d)

Isolated 0.22 g, 39% after hydrogenation of the olefin (Example 13) over 10% Pd on C and column chromatography over silica gel using a mixture of hexanes and EtOAc (3:1) as eluent. IR (film) 1750 cm$^{-1}$; $^1$H NMR (CDCl$_3$) δ3.42 (2H, d of AB q, J=14Hz, J'=7Hz, CH$_2$-Ar), 3.67 (3H, s, OCH$_3$), 3.71 (3H, s, OCH$_3$), 4.19 (1H, t, J=7Hz, CHCO$_2$CH$_3$), 4.51 (2H, s, OCH$_2$), 6.69 (1H, dd, J=7Hz, J'=2Hz, aromatic H ortho to O), 6.73 (1H, d, J=7Hz, aromatic H ortho to O), 6.82 (1H, d, J=7Hz, aromatic H para to O), 7.14 (1H, t, J=7Hz, aromatic H meta to O), 7.20 to 7.40 (6H, m, aromatic H), 7.40 to 7.60 (4H, m, aromatic H); MS m/z 472 (MH+).

Anal. Calcd. for C$_{28}$H$_{25}$NO$_6$.0.2H$_2$O: C, 70.79; H, 5.39; N, 2.95; H$_2$O, 0.76. Found: C, 70.45; H, 5.31; N, 2.79; H$_2$O, 0.80.

EXAMPLE 16

Methyl α-[[3-(2-hydroxy-2-oxoethoxy)phenyl]methyl]-4,5-diphenyl-2-oxazole acetate (10c)

Isolated 0.75 g, 100% yield after CF$_3$CO$_2$H-induced deprotection of the $^t$Bu ester, mp 122°-127° C. IR (KBr) 2550, 1740 cm$^{-1}$; $^1$H NMR (CDCl$_3$) δ3.38 (2H, d of AB q, J=14Hz, J'=7Hz, CH$_2$Ar), 3.64 (3H, s, CO$_2$CH$_3$), 4.18 (1H, t, J=7Hz, CHCO$_2$Me), 4.45 (2H, s, OCH$_2$), 6.69 (1H, dd, J=7Hz, aromatic H ortho to O), 6.76 (2H, m, aromatic H ortho and para to O), 7.10 (1H, t, J=7Hz, aromatic H meta to O), 7.20 to 7.30 (6H, m, aromatic H), 7.45 to 7.55 (4H, m, aromatic H); MS m/z 458 (MH+).

Anal. Calcd. for C$_{27}$H$_{23}$NO$_6$: C, 70.89; H, 5.07; N, 3.07. Found: C, 71.26; H, 4.95; N, 3.11.

EXAMPLE 17

1-Methylethyl-4,5-diphenyl-2-oxazoleacetate

Sodium (80 mg, 3.5 mg atom) was dissolved in isopropanol (21 mL) and ethyl-4,5-diphenyl-2-oxazoleacetate (1.00 g, 3.2 mmol) added. The mixture was heated at reflux for about 1.5 hours, cooled and concentrated. The residue was diluted with water, acidified to pH=2 with 1N HCl solution and extracted with CH$_2$Cl$_2$. The combined extracts were dried over MgSO$_4$, the solvent removed and the residue chromatographed or a column of silica gel. Elution with a mixture of hexanes and EtOAc (9:1) gave the title compound (0.57 g, 54%). IR (film) 1740 cm$^{-1}$; $^1$H NMR (CDCl$_3$) δ1.26 (6H, d, J=6Hz, CO$_2$CH(CH$_3$)$_2$), 3.89 (2H, s, CH$_2$CO$_2$$^i$Pr), 5.08 (1H, septuplet, OCH(CH$_3$)$_2$), 7.25 to 7.40 (6H, m, aromatic H), 7.50 to 7.65 (4H, m, aromatic H); MS m/z 322 (MH+).

Anal. Calcd. for C$_{20}$H$_{19}$NO$_3$: C, 74.75; H, 5.96; N, 4.36. Found: C, 75.09; H, 5.71; N, 4.18.

EXAMPLE 18

(E) and (Z)-1-methylethyl α-[[3-[2-(1,1,-dimethylethoxy)-2-oxoethoxy]phenyl]-methylene]-4,5-diphenyl-2-oxazoleacetate, (7e)

Isolated 1.42 g, 84% after chromatography on silica gel using hexanes/EtOAc (17:3) as eluent. IR (film) 1755, 1730 cm$^{-1}$; $^1$H NMR (CDCl$_3$) δ1.27 to 1.32 (12H, 2d, J=6Hz, CH(CH$_3$)$_2$), 1.33 and 1.47 (18H, 2s, OC(CH$_3$)$_3$), 4.31 and 4.50 (4H, 2s, OCH$_2$), 5.19 and 5.33 (2H, 2 septuplets, OCH(CH$_3$)$_2$), 6.70 to 7.40 (20H, m, aromatic H), 7.50 to 7.70 (9H, m, aromatic H+olefinic H of (Z) isomer), 8.03 (1H, s, olefinic H of (E) isomer); MS m/z 484 (MH+).

Anal. Calcd. for C$_{33}$H$_{33}$NO$_6$: C, 73.46; H, 6.17; N, 2.60. Found: C, 74.05; H, 6.16; N, 2.78.

EXAMPLE 19

(E) and (Z) 1-Methylethyl α-[[3-[2-(methoxy-2-oxoethoxy)phenyl]methylene]-4,5-diphenyl-2-oxazoleacetate, (7f)

Yield: 0.83 g, 76%. IR (film) 1760, 1730 cm$^{-1}$; $^1$H NMR (CDCl$_3$) δ1.25 to 1.33 (12H, 2d, J=6Hz, OCH(CH$_3$)$_2$), 3.64 and 3.80 (6H, 2s, OCH$_3$), 4.44 and 4.63 (4H, 2s, OCH$_2$), 5.20 and 5.33 (2H, 2 septuplets, OCH(CH$_3$)$_2$), 6.80 to 7.40 (20H, m, aromatic H), 7.50 to 7.80 (9H, m, aromatic H+olefinic H of (Z) isomer), 8.03 (1H, s, olefinic H of (E) isomer); MS m/z 498 (MH+).

Anal. Calcd. for C$_{30}$H$_{27}$NO$_6$.0.1H$_2$O: C, 72.17; H, 5.50; N, 2.81; H$_2$O, 0.36. Found: C, 71.93; H, 5.46; N, 2.78; H$_2$O, 0.20.

EXAMPLE 20

1-Methylethyl α-[[3-[2-(1,1-dimethylethoxy)-2-oxoethoxy)phenyl]methyl]-4,5-diphenyl-2-oxazoleacetate, (9e)

Yield: 0.80 q, 100% after catalytic hydrogenation of the olefin. IR (film) 1755, 1740 cm$^{-1}$; $^1$H NMR (CDCl$_3$) δ1.13 (3H, d, J=6Hz, OCH(CH$_3$)$_2$), 1.20 (3H, d, J=6Hz, OCH(CH$_3$)$_2$), 3.42 (2H, 2d, J=7Hz, CH$_2$Ar), 4.17 (1H, t, J=7Hz, CHCO$_2^i$Pr), 4.44 (2H, s, OCH$_2$), 5.02 (1H, septuplet, J=6Hz, OCH(CH$_3$)$_2$), 6.73 (1H, dd, J=7Hz, J'=2Hz, aromatic H of ortho to O), 6.78 (1H, d, J=2Hz, aromatic H ortho to O), 6.87 (1H, d, J=7Hz, aromatic H para to O), 7.17 (1H, t, J=7Hz, aromatic H meta to O), 7.30 to 7.40 (6H, m, aromatic H), 7.50 to 7.65 (4H, m, aromatic H); MS m/z 542 (MH$^+$).

Anal. Calcd. for C$_{33}$H$_{35}$NO$_6$: C, 73.20; H, 6.47; N, 2.59. Found: C, 73.97; H, 6.76; N, 2.46.

EXAMPLE 21

1-Methylethyl α-[[3-(2-methoxy)-2-oxoethoxy)phenyl]methyl]-4,5-diphenyl-2-oxazoleacetate, (9f)

Isolated 0.55 g, 60% after catalytic hydrogenation of the unsaturated precursor. IR (film) 1760, 1735 cm$^{-1}$; $^1$H NMR (CDCl$_3$) δ1.09(3H, d, J=6Hz, OCH(CH$_3$)$_2$), 1.15 (3H, d, J=6Hz, OCH(CH$_3$)$_2$), 3.39 (2H, 2d, J=7Hz, CH$_2$Ar), 3.71 (3H, s, OCH$_3$), 4.13 (1H, t, J=7Hz, CHCO$_2^i$Pr), 4.52 (2H, s, OCH$_2$), 4.98 (1H, septuplet, J=6Hz, OCH(CH$_3$)$_2$), 6.70 (1H, dd, J=7Hz, J'=2Hz, aromatic H of ortho to O), 6.75 (1H, d, J=2Hz, aromatic H ortho to O), 6.84 (1H, d, J=7Hz, aromatic H para to O), 7.13 (1H, t, J=7Hz, aromatic H meta to O), 7.30 to 7.40 (6H, m, aromatic H), 7.47 to 7.60 (4H, m, aromatic H); MS m/z 500 (MH$^+$).

Anal. Calcd. for C$_{30}$H$_{29}$NO$_6$: C, 72.13; H, 5.86; N, 2.81, Found: C, 71.93; H, 6.03; N, 2.62.

EXAMPLE 22

1-Methylethyl α-[[3-[2-(hydroxy-2-oxoethoxy)phenyl]methyl]-4,5-diphenyl-2-oxazoleacetate, (10d)

Isolated 0.45 g, 77% after dissolution of the tert-methyl ester precursor in CF$_3$CO$_2$H and chromatography on silica gel using CHCl$_3$ and MeOH (95:5) as eluent, mp 88°–93° C. IR (KBr) 1740 cm$^{-1}$; $^1$H NMR (CDCl$_3$) δ1.14 (3H, d, J=6Hz, OCH(CH$_3$)$_2$), 1.21 (3H, d, J=6Hz, OCH(CH$_3$)$_2$), 3.43 (2H, d of ABq, J=14Hz, J'=7Hz, CH$_2$Ar), 4.34 (1H, t, J=7Hz, CHCO$_2^i$Pr), 4.57 (2H, s, OCH$_2$), 5.03 (1H, septuplet, J=6Hz, OCH(CH$_3$)$_2$), 6.75 (1H, dd, J=7Hz, J'=2Hz, aromatic H of ortho to O), 6.83 (2H, m, aromatic H ortho and para to O), 7.16 (1H, t, J=7Hz, aromatic H meta to O), 7.30 to 7.40 (6H, m, aromatic H), 7.50 to 7.60 (4H, m, aromatic H); MS m/z 486 (MH$^+$).

Anal. Calcd. for C$_{29}$H$_{27}$NO$_6$.0.3H$_2$O: C, 70.95; H, 5.67, N; 2.86; H$_2$O, 1.10. Found: C, 70.58; H, 5.67; N, 2.61; H$_2$O, 0.44.

EXAMPLE 23

4,5-Diphenyl-2-oxazoleacetamide

A mixture of ethyl 4,5-diphenyl-2-oxazoleacetate (10.24 g, 33 mmol) and ammonia (35 mL) was heated in a bomb at about 130° C. for about 24 hours. After evaporation of the NH$_3$, the residue was chromatographed on a column of silica gel using EtOAc/hexanes (4:1) as eluent to give the title compound (3.21 g, 34%), mp 129°–133° C. IR (KBr) 3340, 3200, 1665 cm$^{-1}$; $^1$H NMR (CDCl$_3$) δ3.83 (2H, s, CH$_2$CONH$_2$), 7.27 to 7.40 (6H, m, aromatic H), 6.50 to 6.68 (4H, m, aromatic H); MS m/z 279 (MH$^+$).

Anal. Calcd. for C$_{17}$H$_{14}$NO$_2$: C, 73.37; H, 5.08; N, 10.07. Found: C, 73.02; H, 5.04; N, 10.09.

EXAMPLE 24

(E) and (Z) Methyl [3-[3-amino-2-(4,5-diphenyl)-2-oxazolyl]-3-oxo-1-propenyl]phenoxy]acetate (7g)

Prepared from the acid by acid catalyzed esterification and isolated as a foam after chromatography (0.57 g, 52%), mp 69°–76° C. IR (KBr) 420, 1760, 1680 cm$^{-1}$; $^1$H NMR (CDCl$_3$) δ1.55 (0.6H, s, H$_2$O), 3.72 (3H, s, CO$_2$CH$_3$), 3.82 (3H, s, OCH$_3$), 4.53 (2H, s, OCH$_2$), 4.64

(2H, s, OCH$_2$), 6.80 to 7.00 (4H, m, aromatic H), 7.10 to 7.45 (16H, m, aromatic H), 7.55 to 7.70 (9H, m, aromatic H+olefinic H of (Z) isomer), 8.37 (1H, s, olefinic H of (E) isomer); MS m/z 455 (MH+).

Anal. Calcd. for C$_{27}$H$_{22}$N$_2$O$_5$.0.3H$_2$O: C, 70.52; H, 4.96, N; 6.10; H$_2$O, 1.18. Found: C, 70.76; H, 4.94; N, 5.95; H$_2$O, 1.21.

EXAMPLE 25

(t-Butyl [3-3-amino-2-(4,5-diphenyl-2-oxazolyl)-3-oxopropyl]-phenoxy acetate (9g)

Isolated 0.46 g, 58% as a beige solid, mp 53°-63° C., after chromatography on a column of silica gel using hexane/EtOAc (11:9) as eluent. IR (KBr) 1755, 1685 cm$^{-1}$; $^1$H NMR (CDCl$_3$) δ1.43 (9H, s, C(CH$_3$)$_3$), 4.44 (2H, d of ABq, J=13Hz, J'8Hz, J"=6Hz, CH$_2$Ar), 4.07 (1H, dd, J=8Hz, J'=6Hz, CHCONH$_2$), 4.39 (2H, s, OCH$_2$CO$_2$H), 5.83 (1H, bs, NH), 6.70 to 6.80 (3H, m, aromatic H ortho and para to O), 7.13 (1H, t, J=7Hz, aromatic H meta to O), 7.19 (1H, bs, NH), 7.30 to 7.40 (6H, m, aromatic H), 7.47 (2H, m, aromatic H), 7.57 (2H, m, aromatic H); MS m/z 499 (MH+).

Anal. Calcd. for C$_{30}$H$_{30}$NO$_2$O$_5$: C, 72.78; H, 6.07, N; 5.62. Found: C, 72.20; H, 6.14; N, 5.53.

EXAMPLE 26

Methyl[3-[α-Amino-2-(4,5-diphenyl-2-oxazolyl)-3-oxo-propyl]phenoxy]acetic acid (9h)

Isolated 0.39 g, 72% as a White foam, mp 48°-55° C., after chroamtography on silica gel. IR (KBr) 1755, 1680 cm$^{-1}$; $^1$H NMR (CDCl$_3$) δ1.58 (s, H$_2$O), 3.45 (2H, d, ABq, J=13Hz, J'=8Hz, J"=6Hz, CH$_2$Ar), 3.73 (3H, s, CO$_2$CH$_3$), 4.06 (1H, dd, J=8Hz, J'=6H, CHCONH$_2$), 4.52 (2H, s, OCH$_2$), 5.50 (1H, bs, CO.NH), 6.70 to 6.80 (3H, m, aromatic H ortho and para to O), 7.15 (1H, t, aromatic H meta to O), 7.25 (1H, bs, CONH), 7.30 to 7.43 (6H, m, aromatic H), 7.47 (2H, m, aromatic H), 7.58 (2H, m, aromatic H); MS m/z 457 (MH+).

Anal. Calcd. for C$_{27}$H$_{24}$N$_2$O$_5$.0.4H$_2$O: C, 69.94; H, 5.40, N; 6.05; H$_2$O, 1.55. Found: C, 70.18; H, 5.26; N, 5.47; H$_2$O, 3.96.

EXAMPLE 27

[3-[3-Amino-2-(4,5-diphenyl-2-oxazolyl)-3-oxopropyl]-phenoxy]acetic acid, (10e)

Isolated 0.28 g, 100% as a foam, mp 80°-84° C. IR (KBr) 3420, 1730, 1675, 1605, 1590 cm$^{-1}$; $^1$H NMR (CDCl$_3$) δ3.42 (2H, d of ABq, J=13Hz, J'=7Hz, CH$_2$Ar), 3.40 (bs, H$_2$O), 4.19 (1H, t, J=7Hz, CHCONH$_2$), 4.57 (2H, s, OCH$_2$), 6.59 (1H, bs, CO.NH), 6.98 (1H, d, J=7Hz, aromatic H ortho to O), 6.79 (2H, m, aromatic H ortho and para to O), 7.11 (1H, t, J=7Hz, aromatic H meta to O), 7.30 to 7.40 (6H, m, aromatic H), 7.45 to 7.60 (4H, m, aromatic H); MS m/z 443 (MH+).

Anal. Calcd. for C$_{26}$H$_{22}$N$_2$O$_5$.0.6H$_2$O: C, 68.90; H, 5.16, N; 6.19; H$_2$O, 2.39. Found: C, 68.83; H, 5.05; N, 5.77; H$_2$O, 5.06.

EXAMPLE 28

(E) and (Z) Methyl [3-[2-(4,5-diphenyl-2-oxazolyl)-3-methylamino-3-oxo-propenyl]phenoxy]acetate, (7h)

Isolated 2.10 g, 22% as a foam after chromatography. IR (KBr) 1765, 1660 cm$^{-1}$; $^1$H NMR (CDCl$_3$) δ1.62 (s, H$_2$O), 2.95 (3H, d, J=5Hz, CH$_3$N); 3.00 (3H, d, J=6Hz, CH$_3$N), 3.72 (3H, s, CO$_2$CH$_3$), 3.82 (3H, s, CO$_2$CH$_3$), 4.52 (2H, s, OCH$_2$), 4.63 (2H, s, OCH$_2$), 6.25 (1H, q, J=5Hz, NH of one isomer), 6.80 to 7.00 (4H, m, aromatic H ortho to O), 7.10 to 7.50 (16H, m, aromatic H), 7.55 to 7.75 (5H, m, aromatic H+olefinic H of (Z) isomer), 8.37 (1H, s, olefinic H of (E) isomer), 8.83 (1H, q, J=5Hz, NH of one isomer); MS m/z 469 (MH+).

Anal. Calcd. for C$_{28}$H$_{24}$N$_2$O$_5$.0.3H$_2$O: C, 70.97; H, 5.24, N; 5.92; H$_2$O, 1.14. Found: C, 71.16; H, 5.01; N, 5.91; H$_2$O, 1.07.

EXAMPLE 29

(E) and (Z)
[3-[2-(4,5-Diphenyl-2-oxazolyl)-3-(methylamino)-3-oxo-propenyl]phenoxy]acetic acid (8d)

Isolated 0.20 g, 40% as a yellow solid, mp 166°-171° C., after chromatography using CHCl3/MeOH (19:1) as eluent. IR (KBr) 3300, 3060, 2940, 1760, 1700, 1650, 1630, 1605 cm$^{-1}$; $^1$H NMR (CDCl3) δ2.50 and 2.58 (3H, d, J=6Hz, ratio 17:3, NH CH3), 4.10 and 4.20 (2U, s, ratio 3:17, OCH2), 6.49 (1H, m, aromatic H ortho to O), 6.60 to 7.10 (9H, m, aromatic H), 7.12 and 7.83 (1H, s, ratio 17:3, olefinic H), 7.15 to 7.30 (4H, m, aromatic H), 7.59 and 8.28 (1H, q, J=6Hz, ratio 17:3, NHCH3); MS m/z 455 (MH+).

Anal. Calcd. for C27H22N2O5.0.7H2O: C, 69.43; H, 5.06, N; 6.00; H2O, 2.70. Found: C, 69.31; H, 4.74; N, 5.26; H2O, 1.49.

EXAMPLE 30

Methyl[3-[2-(4,5-diphenyl-2-oxazolyl)-3-(methylamino)-3-oxo-propyl]phenoxy]acetate (9i)

Isolated 4.27 g, 83% as a light yellow solid, mp 109°-113° C., after chromatography on a column of silica gel using hexanes/EtoAc (1:1) as eluent. IR (KBr) 3300, 3060, 2950, 1760, 1740, 1655 cm$^{-1}$; $^1$H NMR (CDCl3) δ1.68 (s, H2O), 2.80 (3H, d, J=5Hz, CH3NH), 3.30 to 3.55 (2H, d of ABq, J=13Hz, J'=8Hz, J"=6Hz, CH2Ar), 3.73 (3H, s, OCH3), 4.04 (1H, dd, J=8Hz, J'=6Hz, CH.CONHCH3), 4.51 (2H, s, OCH2), 6.65 to 6.80 (3H, s, aromatic H ortho and para to O), 7.10 (1H, m, NH), 7.14 (1H, t, J=7Hz, aromatic H meta to O), 7.30 to 7.40 (6H, m, aromatic H), 7.40 to 7.50 (2H, m, aromatic H), 7.55 to 7.62 (2H, m, aromatic H); MS m/z (MH+).

Anal. Calcd. for C28H26N2O5.0.15H2O: C, 71.07; H, 5.61, N; 5.93; H2O, 0.57. Found: C, 70.75; H, 5.46; N, 5.78; H2O, 0.55.

EXAMPLE 31

[3-[2-(4,5-Diphenyl-2-oxazolyl)-3-(methylamino)-3-oxopropyl]phenoxy]acetic acid, (10f)

Isolated 2.87 g, 100% as a foam, mp 67°-73° C. IR (KBr) 3370, 3060, 2940, 1740, 1650 cm$^{-1}$; $^1$H NMR (CDCl3) δ2.73 (3H, d, J=5Hz, NHCH3), 3.40 (2H, d of ABq, J=13Hz, J'=8Hz, J"=8Hz, CH2Ar), 4.30 (1H, t, J=8Hz, CH.CONHCH3), 4.56 (2H, s, OCH2), 6.65 to 7.00 (4H, m, aromatic H ortho and para to O+NH), 7.10 (1H, t, J=7Hz, aromatic H para to O), 7.15 to 7.40 (6H, m, aromatic H), 7.40 and 7.60 (4H, m, aromatic H); MS m/z 457 (MH+).

Anal. Calcd. for C27H24N2O5.0.4H2O: C, 69.94; H, 5.40, N; 6.05; H2O, 1.56. Found: C, 69.74; H, 5.16; N, 5.86; H2O, 1.53.

EXAMPLE 32

(Z)-Methyl [3-[3-(dimethylamino)-2-(4,5-diphenyl-2-oxazolyl)-3-oxo-1-propenyl]phenoxy]acetate, (7i)

Isolated 4.80 g, 61% as yellow crystals after chromatography and recrystallization from hexane/CH2Cl2 (3:1), mp 159°-162.5° C. IR (KBr) 1760, 1635 cm$^{-1}$; $^1$H NMR (CDCl3) δ2.91 (3H, s, NCH3), 3.13 (3H, s, NCH3) 3.80 (3H, s, OCH3), 4.62 (2H, s, OCH2), 5.26 (s, CH2Cl2), 6.91 (1H, dd, J=7Hz, J'=2Hz, aromatic H ortho to O), 7.05 (1H, d, J=2Hz, aromatic H ortho to O), 7.14 (1H, d, J=8Hz, aromatic H para to O), 7.20 to 7.43 (7H, m, aromatic H), 7.54 (1H, s, olefinic H), 7.55 to 7.75 (4H, m, aromatic H); $^{13}$C NMR δ157.6 (d, J=8.1Hz, O—C=N, indicative of the (Z) configuration; MS m/z 483 (MH+).

Anal. Calcd. for C29H26N2O5.0.2CH2Cl2: C, 70.22; H, 5.33, N; 5.61. Found: C, 70.14; H, 5.34; N, 5.55.

EXAMPLE 33

(Z)-[3-[3-(Dimethylamino)-2-(4,5-diphenyl-2-oxazolyl)-3-oxo-1-propenyl]phenoxy]acetic acid, (8e)

Isolated 0.91 g, 92% after recrystallization from CH$_2$Cl$_2$/hexanes/MeOH (2:1:0.5), mp 223°–226.5° C. IR (KBr) 3450, 3060, 2940, 1755, 1740, 1640 cm$^{-1}$; $^1$H NMR (DMSO-d$_6$) δ2.88 (3H, s, NCH$_3$), 3.03 (3H, s, NCH$_3$), 3.31 (1H, bs, CO$_2$H), 4.67 (2H, s, OCH$_2$), 6.95 (1H, dd, J=7Hz, J'=2Hz, aromatic H ortho to O), 7.00 to 7.15 (2H, m, aromatic H ortho and para to O), 7.34 (1H, t, J=7Hz, aromatic H meta to O), 7.40 to 7 55 (6H, m, aromatic H), 7.55 to 7.70 (5H, m, aromatic H+olefinic H); $^{13}$C δ157.6 (d, J=8.2Hz, O—C=N, indicative of (Z) geometry); MS m/z 469 (MH+).

Anal. Calcd. for C$_{28}$H$_{24}$N$_2$O$_5$.0.4H$_2$O: C, 70.70; H, 5.26, N; 5.89; H$_2$O, 1.52. Found: C, 70.52; H, 5.11; N, 5.78; H$_2$O, 1.73.

EXAMPLE 34

Methyl [[3-[3-(dimethylamino)-2-(4,5-diphenyl-2-oxazolyl)-3-oxopropyl)phenoxy]acetate, (9j)

Isolated 1.95 g, 77% as an oil after chromatography on silica gel using EtOAc/hexanes (1:1) as eluent. IR (film) 3000, 2940, 1755, 1650 cm$^{-1}$, $^1$H NMR (CDCl$_3$) δ2.93 (3H, s, NCH$_3$), 2.99 (3H, s, NCH$_3$), 3.45 (2H, d of ABq, J=13.5Hz, J'=8.5Hz, J''=6.5Hz, CH$_2$Ar), 3.76 (3H, s, OCH$_3$), 4.45 (1H, dd, J=8.5Hz, J'=6.5Hz, CH.CON), 4.56 (2H, s, OCH$_2$), 6.76 (1H, dd, J=8Hz, J'=2Hz, aromatic H ortho to O), 6.79 (1H, d, J=2Hz, aromatic H ortho to O), 6.87 (1H, d, J=8Hz, aromatic H para to O), 7.17 (1H, t, J=8Hz, aromatic H meta to O), 7.30 to 7.40 (6H, m, aromatic H), 7.50 to 7.70 (4H, m, aromatic H); MS m/z 485 (MH+).

Anal. Calcd. for C$_{29}$H$_{28}$N$_2$O$_5$.0.2H$_2$O: C, 71.36; H, 5.87, N; 5.74; H$_2$O, 0.74. Found: C, 71.68; M, 5.82; N, 5.14; H$_2$O, 0.81.

EXAMPLE 35

[3-[3-(Dimethylamino)-2-(4,5-diphenyl-2-oxazolyl)-3-oxopropyl]phenoxy]acetic acid, (10g)

Isolated 1.28 g, 90% as a foam, mp 76°–80° C. IR (KBr) 3420, 2930, 1735, 1650, 1620 cm$^{-1}$; $^1$H NMR (CDCl$_3$) δ2.92 (3H, s, NHCH$_3$), 2.99 (3H, s, NCH$_3$), 3.42 (2H, d, of ABq, J=13.5Hz, J'=8Hz, CH$_2$Ar), 3.92 (1H, bs, H$_2$O), 4.55 (2H, s, OCH$_2$), 4.72 (2H, t, J=8Hz, CH$_2$Ar), 6.75 to 6.87 (3H, m, aromatic H ortho and para to O), 7.13 (1H, t, J=7Hz, aromatic H meta to O), 7.30 to 7.40 (6H, m, aromatic H), 7.45 and 7.60 (4H, m, aromatic H); MS m/z 471 (MH+).

Anal. Calcd. for C$_{28}$H$_{26}$N$_2$O$_5$.0.4H$_2$O: C, 7 .40; H, 5.66, N; 5.87; H$_2$O, 1.51. Found: C, 70.35; H; 5.30; N, 5.71; H$_2$O 3.76.

EXAMPLE 36

(E)-Methyl[3-[2-cyano-2-(4,5-diphenyl-2-oxazolyl) ethenyl]phenoxy]acetate, (16)

Isolated 1.28 g, 59%, mp 152°–153° C., after chromatography and subsequent recrystallization from CH$_2$Cl$_2$/hexanes (1:1). IR (KBr) 2230, 1745 cm$^{-1}$; $^1$H NMR (CDCl$_3$) δ3.82 (3H, s, CO$_2$CH$_3$), 4.71 (2H, s, OCH$_2$), 7.08 (1H, dd, J=7Hz, J'=2Hz, aromatic H ortho to O), 7.25 to 7.40 (13H, m, aromatic H), 7.45 to 7.75 (6H, m, aromatic H), 8.10 (1H, s, olefinic H), $^{13}$C NMR δ155.7 (d, J=7.8Hz, O—C=N, indicative of (E) geometry); MS m/z 437 (MH+).

Anal. Calcd. for C$_{27}$H$_{20}$N$_2$O$_4$: C, 74.31; H, 4.62, N; 6.42. Found: C, 74.19; H; 4.61; N, 6.34.

EXAMPLE 37

(E)-[3-[2-cyano-2-(4,5-diphenyl-2-oxazolyl) ethenyl]phenoxy]acetic acid (17)

Isolated 0.46 g, 63% mp 154°–159° C. after recrystallization from hexane/CH$_2$Cl$_2$ (5:1). IR (KBr) 3450, 2240, 1740, 1550, 1530 cm$^{-1}$; $^1$H NMR (CDCl$_3$) δ4.50 (bs, H$_2$O+CO$_2$H), 4.64 (2H, s, OCH$_2$), 7.02 (1H, dd, J=7Hz, J'=2Hz, aromatic H ortho to O), 7.10 to 7.80 (13H, m, aromatic H), 7.98 (1H, s, olefinic H); MS m/z 423 (MH+) (FAB).

Anal. Calcd. for C$_{26}$H$_{18}$N$_2$O$_4$.0.6H$_2$O: C, 72.09; H, 4.47, N; 6.47; H$_2$O, 2.50. Found: C, 71.90; H; 4.27; N, 6.32; H$_2$O, 1.76.

EXAMPLE 38

Methyl[3-[2-(cyano-2-(4,5-diphenyl-2-oxazolyl)ethyl)phenoxy]acetate (18)

Sodium borohydride (90 mg, 2.3 mmol) was added to a stirred suspension of methyl [3-[2-cyano-2-(4,5-diphenyl-2-oxazolyl)ethenyl]phenoxy]acetate (500 mg, 1.15 mmol) in methanol (10 mL), After about 3 hours, NaBH$_4$ (50 mg, 1.3 mmol) was added and the mixture stirred at room temperature for about 20 hours before being poured onto saturated NH$_4$Cl solution. The mixture was extracted with CH$_2$Cl$_2$. the extracts dried, concentrated and the residue chromatographed on a column of silica gel using hexanes/EtOAc (4:1) as eluent to afford the title compound (0.25 g, 50%) as an oil. IR (KBr) 2250, 1760 cm$^{-1}$; $^1$H NMR (CDCl$_3$) δ3.42 (2H, d of ABq, J=13.7Hz, J'=9Hz, J''=6Hz, CH$_2$Ar), 3.76 (3H, s, CO$_2$CH$_3$), 4.32 (1H, dd, J=8Hz, J'=6Hz, CHCN), 4.59 (2H, s, OCH$_2$), 6.70 to 6.95 (2H, m, aromatic H ortho and para to O), 7.20 to 7.45 (7H, m, aromatic H), 7.50 to 7.70 (4H, m, aromatic H); MS m/z 439 (MH+).

Anal. Calcd. for C$_{27}$H$_{22}$N$_2$O$_4$.0.2H$_2$O: C, 73.36; H, 5.11, N; 6.34; H$_2$O, 0.82. Found: C, 73.49; H, 5.13; N, 6.21; H$_2$O, 0.84.

EXAMPLE 39

[3-[2-Cyano-2-(4,5-diphenyl-2-oxazolyl)ethyl]phenoxy]acetic acid (19)

Isolated 0.24 g, 45%, mp 166°–171° C., after recrystallization from CH$_2$Cl$_2$/hexanes. IR (KBr) 3450, 2250, 1745 cm$^{-1}$; $^1$H NMR (DMSO-d$_6$) δ3.40 (2H, d of ABq, J=13Hz, J'=8.5Hz, J''=6.5Hz, ArCH$_2$), 3.40 (1H, bs, H$_2$O+CO$_2$H), 4.61 (2H, s, OCH$_2$), 5.17 (1H, dd, J=8.5Hz, J'=6.5Hz, CHCN), 6.75 to 7.00 (3H, m, aromatic H ortho and para to O), 7.24 (1H, t, J=7Hz, aromatic H meta to O), 7.25 to 7.70 (10H, m, aromatic H); MS m/z 425 (MH+).

Anal. Calcd. for C$_{26}$H$_{20}$N$_2$O$_4$.1.5H$_2$O: C, 69.18; H, 5.14, N; 6.21; H$_2$O, 5.99. Found: C, 69.38; H; 4.38 N, 5.36; H$_2$O, 1.24. Hig res. MS: C$_{26}$H$_{20}$N$_2$O$_4$ requires 425.1501. Found: 425.1492.

What is claimed is:

1. The compound having the formula wherein
Y and Z are independently hydrogen or together form a bond;
X is CN, CO$_2$R$^1$ or CO.NR$^2$R$^3$;
R and R$^1$ are independently or together H, Na, or C$_1$–C$_5$ lower alkyl;
R$^2$ and R$^3$ are independently or together H, or C$_1$–C$_5$ lower alkyl;
or alkali metal salt thereof.

2. The compound of claim 1 which is (E) ethyl α-[[3-[[(1,1-dimethylethoxy)carbonyl]methoxy) phenyl]methylene]-4,5-diphenyl-2-oxazole acetate.

3. The compound of claim 1 or a pharmaceutically acceptable salt thereof which is (Z) ethyl α-[[3-[[(1,1-dimethylethoxy)carbonyl]methoxy) phenyl]methylene]-4,5-diphenyl-2-oxazole acetate.

4. The compound of claim 1 which is (E) ethyl α-[[3-carboxymethoxy)phenyl]methylene]-4,5-diphenyl-2-oxazole acetate.

5. The compound of claim 1 which is (Z) ethyl α-[[3-carboxymethoxy)phenyl]methylene]-4,5-diphenyl-2-oxazole acetate.

6. The compound of claim 1 which is ethyl α-[[3-hydroxy-2-oxoethoxy)phenyl]methyl]-4,5-diphenyl-2-oxazole acetate.

7. The compound of claim 1 which is (E)-α [[3-(2-hydroxy-2-oxoethyl)phenyl]methylene]-4,5-diphenyl-2-oxazole-acetic acid.

8. The compound of claim 1 which is (Z)-α [[3-(2-hydroxy-2-oxoethyl)phenyl]methylene]-4,5-diphenyl-2-oxazole-acetic acid.

9. The compound of claim 1 which is ethyl α-[(3-[(methoxycarbonyl)methoxy]phenyl]-methyl]-4,5-diphenyl-2-oxazole acetate 10. The compound of claim 1 which is (Z)-ethyl-α-[[3-(2-methoxy-2-oxoethoxy)phenyl]methylene]-4,5-diphenyl-2-oxazole acetate.

11. The compound of claim 1 which is (E)-ethyl α-[[3-(2-methoxy-2-oxoethoxy)phenyl]methylene]-4,5-diphenyl-2-oxazole acetate.

12. The compound of claim 1 which is α-[[3-(2-hydroxy-2-oxoethoxy)phenyl]methyl]-4,5-diphenyl-2-oxazoleacetic acid, disodium salt.

13. The compound of claim 1 which is methyl (E) α-[[3-(2-methoxy-2-oxoethoxy)phenyl]methylene]-4,5-diphenyl-2-oxazoleacetate.

14. The compound of claim 1 which is methyl (Z) α-[[3-(2-methoxy-2-oxoethoxy)phenyl]methylene]-4,5-diphenyl-2-oxazoleacetate.

15. The compound of claim 1 which is methyl α-[[3-(2-methoxy-2-oxoethoxy)phenyl]methyl]-4,5-diphenyl-2-oxazole acetate.

16. The compound of claim 1 or a pharmaceutically acceptable salt thereof which is methyl α-[[3-(2-hydroxy-2-oxoethoxy)phenyl]methyl]-4,5-diphenyl-2-oxazole acetate.

17. The compound of claim 1 which is (E) 1-methylethyl α-[[3-[2-(methoxy-2-oxoethoxy)phenyl]-methylene]-4,5-diphenyl-2-oxazoleacetate.

18. The compound of claim 1 which is (Z) 1-methylethyl α-[[3-[2-(methoxy-2-oxoethoxy)phenyl]-methylene]-4,5-diphenyl-2-oxazoleacetate.

19. The compound of claim 1 which is 1-methylethyl α-[[3-[2-(1,1-dimethylethoxy)-2-oxoethoxy)phenyl]methyl]-4,5-diphenyl-2-oxazoleacetate.

20. The compound of claim 1 which is 1-methylethyl α-[[3-(2-methoxy)-2-oxoethoxy)phenyl]methyl]-4,5-diphenyl-2-oxazoleacetate.

21. The compound of claim 1 which is 1-methylethyl α-[[3-[2-(hydroxy-2-oxoethoxy)phenyl]methyl]-4,5-diphenyl-2-oxazoleacetate.

22. The compound of claim 1 which is (E) methyl[3-[3-amino-2-(4,5-diphenyl)-2-oxazolyl]-3-oxo-1-propenyl]phenoxy]acetate.

23. The compound of claim 1 which is (Z) methyl[3-[3-amino-2-(4,5-diphenyl)-2-oxazolyl]-3-oxo-1-propenyl]phenoxy]acetate.

24. The compound of claim 1 which is [3-[3-amino-2-(4,5-diphenyl-2-oxazolyl)-3-oxopropyl]phenoxy]acetic acid.

25. The compound of claim 1 which is (E) methyl[3-[2-(4,5-diphenyl-2-oxazolyl)-3-methylamino-3-oxopropenyl]phenoxy]acetate.

26. The compound of claim 1 which is (Z) methyl[3-[2-(4,5-diphenyl-2-oxazolyl)-3-methylamino-3-oxopropenyl]phenoxy]acetate.

27. The compound of claim 1 which is (E) [3-[2-(4,5-diphenyl-2-oxazolyl)-3-(methylamino)-3-oxopropenyl]phenoxy]acetic acid.

28. The compound of claim 1 which is (Z) [3-[2-(4,5-diphenyl-2-oxazolyl)-3-(methylamino)-3-oxopropenyl]phenoxy]acetic acid.

29. The compound of claim 1 which is methyl[3-[2-(4,5-diphenyl-2-oxazolyl)-3-(methylamino)-3-oxopropyl]phenoxy]acetate.

30. The compound of claim 1 which is [3-[2-(4,5-diphenyl-2-oxazolyl)-3-(methylamino)-3-oxopropyl]-phenoxy]acetic acid.

31. The compound of claim 1 which is (Z)-[3-[3-(dimethylamino)-2-(4,5-diphenyl-2-oxazolyl)-3-oxo-1-propenyl]phenoxy]acetic acid.

32. The compound of claim 1 which is methyl [[3-[3-(dimethylamino)-2-(4,5-diphenyl-2-oxazolyl)-3-oxopropyl]phenoxy]acetate.

33. The compound of claim 1 which is [3-[3-(dimethylamino)-2-(4,5-diphenyl-2-oxazolyl)-3-oxopropyl]phenoxy]acetic acid.

34. The compound of claim 1 which is (E)-methyl[3-[2-cyano-2-(4,5-diphenyl-2-oxazolyl)ethenyl]phenoxy]acetate.

35. The compound of claim 1 which is (E)-[3-[2-cyano-2-(4,5-diphenyl-2-oxazolyl)ethenyl]phenoxy]acetic acid.

36. The compound of claim 1 which is methyl[3-[2-(cyano-2-(4,5-diphenyl-2-oxazolyl)ethyl) phenoxy]acetate.

37. The compound of claim 1 which is [3-[2-cyano-2-(4,5-diphenyl-2-oxazolyl)ethyl]phenoxy]acetic acid.

38. A method for inhibiting blood platelet aggregation in a mammal which comprises administering a therapeutically effective amount of a compound of claim 1 or a pharmaceutically acceptable salt thereof.

39. The pharmaceutical composition for inhibiting blood platelet aggregation comprising a therapeutically effective amount of a compound of claim 1 of a pharmaceutically acceptable acid addition salt thereof and a pharmaceutical carrier.

* * * * *